United States Patent [19]

Crimmin et al.

[11] Patent Number: 5,696,082
[45] Date of Patent: Dec. 9, 1997

[54] HYDROXAMIC ACID DERIVATIVES

[75] Inventors: Michael John Crimmin; Andrew Paul Ayscough; Raymond Paul Beckett, all of Oxford, United Kingdom

[73] Assignee: British Biotech Pharmaceuticals Limited, Oxford, England

[21] Appl. No.: 530,374

[22] PCT Filed: Apr. 18, 1994

[86] PCT No.: PCT/GB94/00808

§ 371 Date: May 28, 1996

§ 102(e) Date: May 28, 1996

[87] PCT Pub. No.: WO94/24140

PCT Pub. Date: Oct. 27, 1994

[30] Foreign Application Priority Data

Apr. 17, 1993 [GB] United Kingdom ............ 9307956

[51] Int. Cl.$^6$ .............. C07K 9/00; C07C 259/06; C07H 13/06; A61K 31/70
[52] U.S. Cl. ................ 514/8; 514/19; 514/575; 562/621; 562/623; 930/DIG. 500
[58] Field of Search ............ 514/8, 19; 562/621, 562/623

[56] References Cited

FOREIGN PATENT DOCUMENTS

92/09563  6/1992  WIPO ............ C07C 259/00

*Primary Examiner*—Cecilia J. Tsang
*Assistant Examiner*—Michael L. Borin
*Attorney, Agent, or Firm*—Banner & Witcoff, Ltd.

[57] ABSTRACT

Compounds of general formula (I) wherein X is —CONHOH or —CO$_2$H, principally characterised by the presence in substituent R$_3$ and/or R$_4$ of a group of formula (II) are inhibitors of matrix metalloproteinases and inhibitors of the production of turnout necrosis factor.

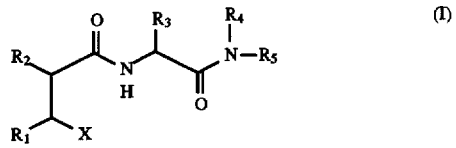

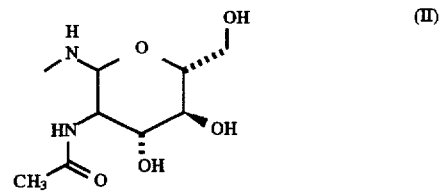

7 Claims, No Drawings

HYDROXAMIC ACID DERIVATIVES

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumour necrosis factor from cells.

BACKGROUND TO THE INVENTION

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth.

Metalloproteinases are characterised by the presence in the structure of a zinc(II) ionic site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (J. F. Woessner, FASEB J, 1991, 5, 2145–2154). Many known MMP inhibitors are peptide derivatives, based on naturally occuring amino acids, and are analogues of the cleavage site in the collagen molecule. A recent paper by Chapman et al J. Med. Chem. 1993, 36, 4293–4301 reports some general structure/activity findings in a series of N-carboxyalkyl peptides. Other known MMP inhibitors are less peptidic in structure, and may more properly be viewed as pseudopeptides or peptide mimetics. Such compounds usually having a functional group capable of binding to the zinc(II) site in the MMP, and known classes include those in which the zinc binding group is a hydroxamic acid, carboxylic acid, sulphydryl, and oxygenated phosphorus (eg phosphinic acid and phosphonic acid) groups.

Two known classes of pseudopeptide or peptide mimetic MMP inhibitors have a hydroxamic acid group or a, carboxylic group respectively as their zinc binding groups. With a few exceptions, such known MMPs may be represented by the structural formula (IA)

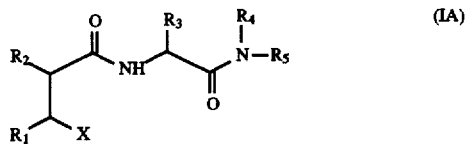

in which X is the zinc binding hydroxamic acid (—CONHOH) or carboxylic acid (—COOH) group and the groups $R_1$ to $R_5$ are variable in accordance with the specific prior art disclosures of such compounds. Examples of patent publications disclosing such structures are given below.

In such compounds, it is generally understood in the art that variation of the zinc binding group and the substituents $R_1$, $R_2$ and $R_3$ can have an appreciable effect on the relative inhibition of the metalloproteinase enzymes. The group X is thought to interact with metalloproteinase enzymes by binding to a zinc(II) ion in the active site. Generally the hydroxamic acid group is preferred over the carboxylic acid group in terms of inhibitory activity against the various metalloproteinase enzymes. However, the carboxylic acid group in combination with other substituents can provide selective inhibition of gelatinase (EP-489,577-A). The $R_1$, $R_2$ and $R_3$ groups are believed to occupy respectively the P1, P1' and P2' amino acid side chain binding sites for the natural enzyme substrate. There is evidence that a larger $R_1$ substituent can enhance activity against stromelysin, and that a $(C_1-C_6)$alkyl group (such as iso-butyl) at $R_2$ may be preferred for activity against collagenase whilst an alkylphenyl group (such as phenylpropyl) at $R_2$ may provide selectivity for gelatinase over the other metalloproteinases.

Pseudopeptide or peptide mimetic MMP inhibitors of formula (IA) with potent in vitro activities are known, but are generally poorly absorbed following oral administration. Although, it is known that a number of factors can influence oral absorption (such as aqueous solubility, pKa, log P and molecular weight) the design of pseudopeptide enzyme inhibitors with high oral absorption is far from straightforward. Finding a combination of $R_1$, $R_2$, $R_3$, $R_4$ or $R_5$ substituents that permits a good balance of intrinsic level of activity, water solubility, oral absobtion, and pharmacokinetic properties is a continuing problem in the art, since those properties can vary in an unpredictable way as the substituents $R_1$–$R_5$ are varied. Identifying hydroxamic and carboxylic acid-based MMP inhibitors having such properties remains a much sought after goal in the art.

Tumour necrosis factor (herein referred to as "TNF") is a cytokine which is produced initially as a cell-associated 28 kD precursor. It is released as an active, 17 kD form, which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

Recently, WO 93/20047 disclosed a class of hydroxamic acid based MMP inhibitors which also are active in inhibiting TNF production.

As mentioned above MMP inhibitors have been proposed with hydroxamic acid or carboxylic acid zinc binding groups. The following patent publications disclose hydroxamic acid-based MMP inhibitors:

U.S. Pat. No. 4,599,361 (Searle)
EP-A-0231081 (ICI)
EP-A-0236872 (Roche)
EP-A-0274453 (Bellon)
WO 90/05716 (British Bio-technology Ltd ("BBL"))
WO 90/05719 (BBL)
WO 91/02716 (BBL)
WO 92/09563 (Glycomed)
EP-A-0497192 (Roche)
WO 92/13831 (BBL)
WO 92/17460 (Smithkline Beecham)
EP-A-0489577 (Celltech)
EP-A-0489579 (Celltech)
WO 92/22523 (Research Corporation Technologies)
U.S. Pat. No. 6,256,657 (Sterling Winthrop)
WO 93/09090 (Yamanouchi)
WO 93/09097 (Sankyo)
WO 93/20047 (BBL)
WO 93/21942 (BBL)
WO 93/24449 (Celltech)
WO 93/24475 (Celltech)
EP-A-0574758 (Roche)
EP-A-0575844 (Roche)
WO 94/02446 (BBL)
WO 94/02447 (BBL)

The following patent publications disclose carboxylic acid-based MMP inhibitors:

EP-A-0489577 (Celltech)
EP-A-0489579 (Celltech)
WO 93/24449 (Celltech)
WO 93/24475 (Celltech)

BRIEF DESCRIPTION OF THE INVENTION

This invention makes available a novel group of compounds of formula (IA), wherein X is a hydroxamic acid or carboxylic acid group, whose novel characterising feature is carbohydrate moiety in one or both of the groups $R_3$ and $R_4$. The compounds of the invention have good intrinsic activity as inhibitors of the enzymes collagenase, gelatinase and stromelysin, and inhibit the production of the pro-inflammatory cytokine TNF. The compounds also have useful pharmacokinetic properties, including bioavailability after oral administration.

DETAILED DESCRIPTION OF THE INVENTION

According to a first aspect of the invention there is therefore provided a compound of general formula (I):

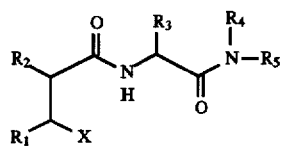

wherein;

X is —CONHOH or —$CO_2H$;

$R_1$ is hydrogen, a $C_1$–$C_6$ alkyl, $C_2$–$C_6$ alkenyl, phenyl, substituted phenyl, phenyl($C_1$–$C_6$ alkyl), heterocyclyl, substituted heterocyclyl, heterocyclyl($C_1$–$C_6$ alkyl), substituted heterocyclyl($C_1$–$C_6$ alkyl), or a group $BSO_nA$— wherein n is 0, 1 or 2 and B is hydrogen or a ($C_1$–$C_6$) alkyl, phenyl, substituted phenyl, heterocyclyl, $C_1$–$C_6$ acyl, phenacyl or substituted phenacyl group, and A represents $C_1$–$C_6$ alkyl; amino; protected amino; acylamino; OH; SH; $C_1$–$C_6$ alkoxy; $C_1$–$C_6$ alkylamino; $C_1$–$C_6$ alkylthio; aryl($C_1$–$C_6$ alkyl); amino($C_1$–$C_6$ alkyl); hydroxy($C_1$–$C_6$ alkyl), mercapto ($C_1$–$C_6$ alkyl) or carboxy($C_1$–$C_6$ alkyl) wherein the amino-, hydroxy-, mercapto- or carboxyl-group are optionally protected or the carboxyl-group amidated; lower alkyl substituted by maleimido, succinimido, naphthalimido, 2,3-dihydro-1,3-dioxo-1H-benz[d,e] isoquinol-2-yl, carbamoyl, mono(lower alkyl) carbamoyl, di(lower alkyl)carbamoyl, di(lower alkyl) amino, carboxy-lower alkanoylamino, pyrrolidino or morpholino;

$R_2$ is a ($C_1$–$C_6$)alkyl, ($C_2$–$C_6$)alkenyl, ($C_2$–$C_6$)alkynyl, phenyl($C_1$–$C_6$)alkyl, heteroaryl($C_1$–$C_6$)alkyl, cycloalkyl ($C_1$–$C_6$)alkyl or cycloalkenyl ($C_1$–$C_6$) alkyl group anyone of which may be optionally substituted by one or more substituents selected from ($C_1$–$C_{10}$) alkyl, O($C_1$–$C_6$) alkyl, S($C_1$–$C_6$) alkyl, O($C_1$–$C_6$ alkyl) O$C_1$–$C_6$ alkyl, S($C_1$–$C_6$ alkyl)O$C_1$–$C_6$ alkyl, O($C_1$–$C_6$ alkyl)S$C_1$–$C_6$ alkyl or S($C_1$–$C_6$ alkyl)S$C_1$–$C_6$ alkyl;

$R_3$ is (a) a group —($C_1$–$C_6$ alkyl)$COR_6$, or —($C_1$–$C_6$ alkyl)($C_6H_4$ )$XR_6$ where X is a group —$OCH_2CO$, —CO—, —$CH_2CH_2CO$— or —$NHCH_2CO$— and $R_6$ is a group of formula (II):

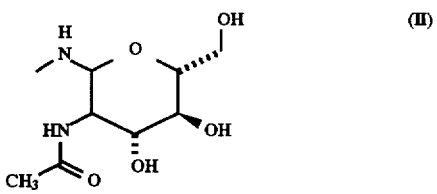

or (b) (subject to the proviso below) the side chain of a naturally occurring amino acid, which may be protected if functional groups are present, eg by acylation of amino groups and amidation of carboxyl groups; or a group $CR_8R_9R_{10}$ in which each of $R_8$, $R_9$ and $R_{10}$ is independently hydrogen, ($C_1$–$C_6$)alkyl, ($C_2$–$C_6$)alkenyl, ($C_2$–$C_6$)alkynyl, phenyl($C_1$–$C_6$) alkyl, S($C_1$–$C_6$) alkyl, OPh, $OCH_2$Ph, SPh, $SCH_2$Ph, halogen, CN, $CO_2H$, ($C_1$–$C_4$)perfluoroalkyl, $CH_2OH$, $CO_2(C_1$–$C_6)$alkyl, or a group phenyl or heteroaryl which is optionally substituted by one or more substituents independently selected from hydrogen, hydroxyl, halogen, CN, $CO_2H$, $CO_2(C_1$–$C_6)$alkyl, $CONH_2$, $CONH(C_1$–$C_6)$ alkyl, $CONH(C_1$–$C_6$alkyl$)_2$, CHO, $CH_2OH$, ($C_1$–$C_4$) perfluoroalkyl, $O(C_1$–$C_6)$alkyl, $S(C_1$–$C_6)$alkyl, $SO(C_1$–$C_6)$ alkyl, $SO_2(C_1$–$C_6)$alkyl, $NO_2$, $NH_2$, $NH(C_1$–$C_6)$alkyl, $N((C_1$–$C_6)$alkyl$)_2$, $NHCO(C_1$–$C_6)$alkyl, ($C_1$–$C_6)$alkyl, ($C_2$–$C_6$)alkenyl, ($C_2$–$C_6$)alkynyl, ($C_3$–$C_8$)cycloalkyl, ($C_4$–$C_8$)cycloalkenyl, phenyl or benzyl; or $R_8$ and $R_9$ together with the carbon atom to which they are attached form a 3 to 8 membered cycloalkyl or a 5- to 6-membered heterocyclic ring; or $R_8$, $R_9$ and $R_{10}$ together with the carbon atom to which they are attached form a bicyclic ring (for example adamantyl);

$R_4$ is (i) a group —(CH($R_7$)CONH$)_mCOR_6$, wherein m=0, 1, or 2, $R_6$ is as defined above, and $R_7$ is hydrogen or the side chain of a naturally occurring amino acid, which may be protected if functional groups are present, eg by acylation of amino groups and amidation of carboxyl groups; or (ii) (subject to the proviso below) hydrogen, $C_1$–$C_6$ alkyl, ($C_1$–$C_4$)perfluoroalkyl or a group D-($C_1$-$C_6$ alkyl) wherein D represents hydroxy, ($C_1$-$C_6$)alkoxy, ($C_1$-$C_6$)alkylthio, acylamino, optionally substituted phenyl or heteroaryl, $NH_2$, or a mono- or di-($C_1$-$C_6$ alkyl amine;

$R_5$ is hydrogen or a ($C_1$-$C_6$)alkyl group;

provided that at least one of the groups $R_3$ and $R_4$ contains a group $R_6$ as defined above or a salt, hydrate or solvate thereof.

As used herein, the term "side chain of a naturally occurring amino acid" includes the side chains of alanine, arginine, asparagine, aspartic acid, cysteine, cystine, glutamic acid, glycine, histidine, 5-hydroxylysine, 4-hydroxyproline, isoleucine, leucine, lysine, methionine, phenylalanine, proline, serine, threonine, tryptophan, tyrosine, valine, alpha-aminoadipic acid, alpha-amino-n-butyric acid, 3,4-dihydroxyphenylalanine, homoserine, alpha-methylserine, ornithine, pipecolic acid, and thyroxine. The amino acid side chains may be protected; for example the carboxyl groups of aspartic acid, glutamic acid and alpha-aminoadipic acid may be esterified (for example as a $C_1$-$C_6$ alkyl ester), the amino groups of lysine, ornithine, 5-hydroxylysine, 4-hydroxyproline may be converted to amides (for example as a $COC_1$-$C_6$ alkyl amide) or carbamates (for example as a C(=O)O$C_1$-$C_6$ alkyl or C(=O)OCH$_2$Ph carbamate), the hydroxyl groups of 5-hydroxylysine, 4-hydroxyproline, serine, threonine, tyrosine, 3,4-dihydroxyphenylalanine, homoserine, alpha-methylserine and thyroxine may be converted to ethers (for example a $C_1$-$C_6$ alkyl or a ($C_1$-$C_6$ alkyl)phenyl ether) or esters (for example a C(=O)$C_1$-$C_6$ alkyl ester) and the thiol group of cysteine may be converted to thioethers (for example a $C_1$-$C_6$ alkyl thioether) or thioesters (for example a C(=O)$C_1$-$C_6$ alkyl thioester).

The unqualified term "heterocyclyl" or "heterocyclic" refers to a 5–7 membered heterocyclic ring containing one or more heteroatoms selected from S, N and O, and optionally fused to a benzene ring, including for example, pyrrolyl, furyl, thienyl, imidazolyl, oxazolyl, thiazolyl, pyrazolyl, pyridinyl, pyrrolidinyl, pyrimidinyl, morpholinyl, piperizinyl, indolyl, benzimidazole, phthalimido, 1,2-dimethyl-3,5-dioxo-1,2,4-triazolidin-4-yl, 3-methyl-2,5-dioxo-1-imidazolidinyl and 3,4,4-trimethyl-2,5-dioxo-1-imidazolidinyl.

As used herein, the term "heteroaryl" refers to a 5- or 6-membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with up to four substituents, each of which independently may be $C_1$-$C_6$ alkoxy, hydroxy, thio, $C_1$-$C_6$ alkylthio, amino, halo (including fluoro, chloro, bromo and iodo), trifluoromethyl, nitro, —COOH, —$CONH_2$ or —$CONHR^A$ wherein $R^A$ is a $C_1$-$C_6$ alkyl group or the residue of a natural alpha-amino acid.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the $R_1$ and X groups —S,
C atom carrying the $R_2$ group —R,
C atom carrying the $R_3$ group —S, but mixtures in which the above configurations predominate are also contemplated.

The main invention-characterising feature of the compounds of the invention is the presence of the group $R_6$ in at least one of the groups $R_3$ and $R_4$. Otherwise in the compounds of the invention the definitions of the groups $R_1$-$R_5$ are based on groups known from the corresponding positions of known hydroxamic and carboxylic acid-based MMP inhibitors.

Thus, in the compounds of the invention:

$R_1$ may for example be hydrogen, methyl, ethyl, hydroxyl, allyl, or thienylmethylsulfanyl. Presently preferred are compounds in which $R_1$ is hydrogen, hydroxyl or allyl.

$R_2$ may for example be a $C_3$-$C_6$ alkyl, cycloalkyl($C_3$-$C_6$ alkyl), phenyl($C_2$-$C_6$ alkyl), $C_2$-$C_4$ alkoxy($C_1$-$C_3$ alkyl)$_m$ or $C_2$-$C_4$ alkylsulphanyl($C_1$-$C_3$ alkyl)$_m$ group wherein m is 0 or 1. Examples of particular $R_2$ groups include isobutyl, n-pentyl, n-hexyl, n-septyl, n-octyl, cyclohexylpropyl, cyclohexylbutyl, cyclohexylpentyl, phenylethyl, phenylpropyl, phenylbutyl, phenylpentyl, propyloxymethyl and propylsulphanyl. Presently preferred are compounds in which $R_2$ is isobutyl.

(In those cases when $R_3$ does not comprise a group $R_6$) examples of suitable $R_3$ groups include benzyl, isobutyl and t-butyl. Presently preferred are compounds in which $R_3$ is benzyl or t-butyl. Presently most preferred are compounds in which $R_3$ is t-butyl.

(In those cases when $R_4$ does not comprise a group $R_6$) $R_4$ may for example be $C_1$-$C_6$ alkyl, ($C_1$-$C_4$) perfluoroalkyl or a group D-($C_1$-$C_6$ alkyl) wherein D represents hydroxy, ($C_1$-$C_6$)alkoxy, ($C_1$-$C_6$)alkylthio, acylamino, optionally substituted phenyl or heteroaryl. Examples of particular $R_4$ groups include methyl, ethyl, propyl, butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, optionally substituted phenylethyl, phenylpropyl, phenylbutyl and phenylpentyl. Presently preferred are compounds in which $R_4$ is methyl, t-butyl or benzyl. Presently most preferred are compounds in which $R_4$ is methyl.

$R_5$ may for example be hydrogen, methyl or ethyl. Presently preferred are compounds in which $R_5$ is hydrogen.

Interesting compounds of the invention include:

[4-(N-Hydroxyamino)-2R-isobutylsuccinyl]-L-phenylalaninyl-glycinyl-N-(2-acetamido-2-deoxy-β-D-glucopyranosyl)-amide;

[4-(N-Hydroxyamino)-2R-isobutylsuccinyl]-L-phenylalaninyl-glycinyl-glycinyl-N-(2-acetamido-2-deoxy-β-D-glucopyranosyl)-amide;

[4-(N-Hydroxyamino)-2R-isobutylsuccinyl]-O-[(2-acetamido-2-deoxy-β-D-glucopyranosyl)carboxamidomethyl]-L-tyrosine-N-methylamide;

3S-Hydroxy-4-(N-hydroxyamino)-2R-isobutylsuccinyl-L-phenylalaninyl-glycinyl-N-(2-acetamido-2-deoxy-β-D-glucopyranosyl)-amide;

and salts, solvates and hydrates thereof.

A compound of the invention which is especially preferred for its potency in inhibiting the production of TNF is:

[3S-Allyl-4-(N-hydroxyamino)-2R-isobutylsuccinyl]-N4-(2-acetamido-2-deoxy-α-D-glucopyranosyl)-L-glutamine-N-methylamide and salts, solvates and hydrates thereof.

Compounds according to the present invention in which X is a hydroxamic acid group (—CONHOH) may be prepared from compounds of the invention in which X is a carboxylic acid group (—COOH). That process, which forms another aspect of the invention, comprises:

(a) coupling an acid of general formula (III)

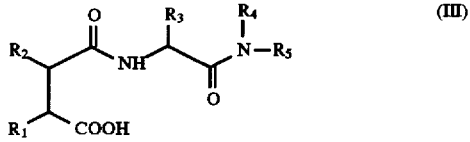

or an activated derivative thereof with hydroxylamine, O-protected hydroxylamine, or a salt thereof, $R_2$, $R_3$, $R_4$, and $R_5$ being as defined in general formula (I) except that any substituents in $R_2$, $R_3$, $R_4$, and $R_5$ which are potentially reactive with hydroxylamine, O-protected hydroxylamine or their salts may themselves be protected from such reaction, then removing any protecting groups from the resultant hydroxamic acid moiety and from any protected substituents in $R_2$, $R_3$, $R_4$, and $R_5$; and (b) optionally converting a compound of general formula (I) into another compound of general formula (I).

Conversion of (III) to an activated intermediate such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, tert-butoxycarbonyl or acetyl groups, or in the form of a phthalimido group. Hydroxy groups, for example those hydroxy groups in the group $R_6$ of the compounds of the invention, may be protected in the above process as readily cleavable ethers such as the tert-butyl or benzyl ether, or as readily cleavable esters such as the acetate. Carboxy groups are often protectable as readily cleavable esters, such as the tert-butyl or benzyl ester.

Compounds of formula (I) above in which the hydroxy groups in the group $R_6$ are protected, for example as the acetate derivatives, are useful intermediates in the preparation of compounds of the invention.

In the special case where $R_1$ in compound (I) is hydroxy, it too may be protected during the coupling of acid (III) with hydroxylamine. In that case a particularly useful technique may be simultaneous protection of the hydroxy group $R_1$ and the adjacent carboxyl group as a dioxalone of formula (IV):

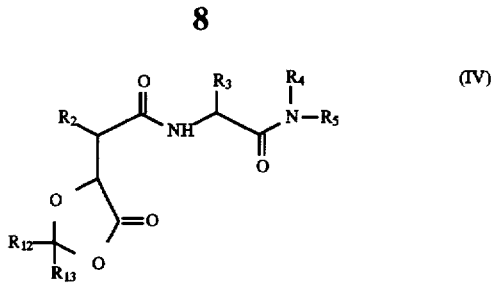

wherein the groups $R_{12}$ and $R_{13}$ are derived from a dioxalone forming reagent, and may be, for example, hydrogen, alkyl, phenyl or substituted phenyl. The dioxalone ring being is opened on reaction with hydroxylamine to give the required hydroxamic acid derivative of formula (I).

Compounds according to the present invention in which X is a carboxylic acid group —COOH may be prepared by a process comprising: coupling an acid of formula (V) or an activated derivative thereof with an amine of formula (VI)

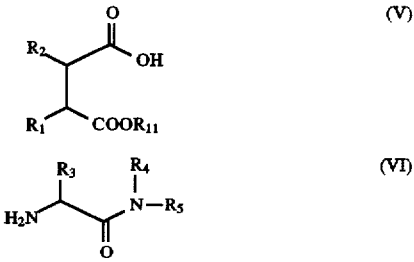

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$, $R_2$, $R_3$, $R_4$, and $R_5$.

Active derivatives of acids (V) include activated esters such as the pentafluorophenyl ester, acid anhydrides and acid halides, eg chlorides. Suitable hydroxy protecting groups may be selected from those known in the art.

In the special case where $R_1$ in compound (V) is hydroxy, it too may be protected during the coupling of compounds (V) and (VI). In that case a particularly useful technique may be simultaneous protection of the two hydroxy groups as a dioxalone of formula (VII):

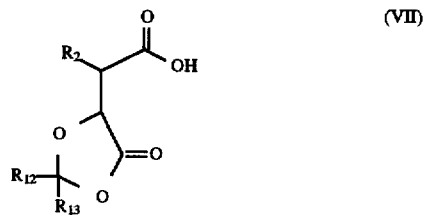

wherein the groups $R_{12}$ and $R_{13}$ are derived from a dioxalone forming reagent, and may be, for example, hydrogen, alkyl, phenyl or substituted phenyl.

As mentioned above, compounds of formula (I) are useful in human or veterinary medicine since they are active as inhibitors of MMPs, and a further advantage lies in their ability to inhibit the release of tumour necrosis factor (TNF) from cells.

Accordingly in another aspect, this invention concerns:
(i) a method of management (by which is meant treatment or prophylaxis) of diseases or conditions mediated by MMPs and/or TNF in mammals, in particular in humans, which method comprises administering to the mammal an effective amount of a compound as defined with respect to formula (I) above, or a pharmaceutically acceptable salt thereof; and (ii) a compound as defined with respect to formula (I) for use in human or veterinary medicine, particularly in the management (by which is meant treatment or prophylaxis) of diseases or conditions mediated by MMPs and/or TNF; and (iii) the use of a compound as defined with respect to formula (I) in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compound of formula (I) together with a pharmaceutically or veterinarily acceptable excipient or carrier. In view of the oral bioavailability advantages of compounds in accordance with the invention, a further aspect of the invention comprises a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The examples which follow illustrate embodiments of the invention but are not intended to limit the scope in any way. The amino acids used in the examples were commercially available or were prepared according to literature procedures.

The following abbreviations have been used throughout:

| | |
|---|---|
| DMF | N, N-Dimethylformamide |
| EDC | N-Ethyl-N'-(3-dimethylaminopropyl)carbodiimide hydrochloride |
| EEDQ | 2-Ethoxy-1-ethoxycarbonyl-1,2-dihydroquinoline |
| HOBt | 1-Hydroxybenzotriazole |
| NMM | N-Methylmorpholine |
| THF | Tetrahydrofuran |
| TFA | Trifluoroacetic acid |
| TLC | Thin layer chromatography |

$^1$H and $^{13}$C NMR spectra were recorded using a Bruker AC 250E spectrometer at 250.1 and 62.9 MHz, respectively. Elemental microanalyses were performed by CHN Analysis Ltd., Alpha House, Countesthorpe Road, South Wigston, Leicester LE8 2PJ, UK.

EXAMPLE 1

[4-(N-Hydroxyamino)-2R-isobutylsuccinyl]-L-phenylalaninyl-glycinyl-N-(2-acetamido-2-deoxy-β-D-glucopyranosyl)-amide

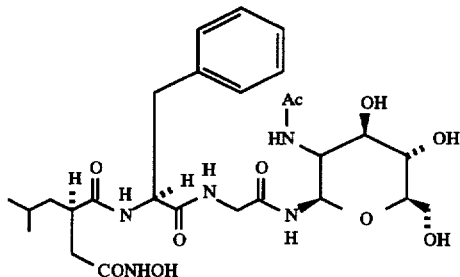

EXAMPLE 1a

N$^{\alpha}$-(Benzyloxycarbonyl)-glycinyl-N-(2-acetamido-3,4,6-tri-O-acetyl-2-deoxy-β-D-glucopyranosyl)-amide N$^{\alpha}$-Benzyloxycarbonyl glycine (2.09 g, 10 mmol) and 1-amino-2-acetamido-3,4,6-tri-O-acetyl-2-deoxy-β-D-glucopyranose (3.46 g, 10 mmol) were dissolved in chloroform (100 ml) and stirred during the addition of EEDQ (2.47 g, 10 mmol) in chloroform (5 ml). The reaction mixture was stirred overnight at room temperature then worked up by washing with hydrochloric acid (1M, 2×100 ml), sodium carbonate (0.5M, 2×100 ml) and saturated brine. The organic layer was dried over magnesium sulphate, filtered and the solvent removed under vacuum to give a white crystalline solid. This material was further purified by recrystallisation from ethyl acetate/methanol (5:1, 180 ml) to yield the title compound (3.32 g, 6.2 mmol, 62%); $^{1}$H NMR: δ ((CD$_{3}$)$_{2}$SO), 8.40 (1H, d, J=8.9 Hz), 7.96 (1H, d, J=9 Hz), 7.44 (1H, t, J=6.1 Hz), 7.36 (5H, s), 5.20–5.07 (2H, m), 5.03 (2H, s), 4.83 (1H, t, J=9.7 Hz), 4.20–3.80 (4H, m), 3.33 (2H, m), 2.00 (3H, s), 1.97 (3H, s), 1.92 (3H, s), and 1.77 (3H, s); $^{13}$C NMR δ ((CD$_{3}$)$_{2}$SO), 172.2, 171.5, 170.7, 170.4, 168.5, 156.4, 136.1, 128.5, 128.1, 80.0, 77.5, 77.0, 76.5, 73.4, 72.7, 63.0, 62.2, 61.2, 52.9, 44.4, 22.9, 20.7 and 20.5.

EXAMPLE 1b

N$^{6\alpha}$-(Benzyloxycarbonyl)-phenylalaninyl-glycinyl-N-(2-acetamido-3,4,6-tri-O-acetyl-2-deoxy-β-D-glucopyranosyl)-amide N-(Benzyloxycarbonyl)-glycinyl-N-(2-acetamido-3,4,6-tri-O-acetyl-2-deoxy-β-D-glucopyranosyl)-amide (3 g, 5.6 mmol) was suspended in methanol and 10% palladium on charcoal (100 mg) added as a slurry in ethyl acetate. Hydrogen gas was passed through the solution for 90 minutes after which time TLC (10% methanol/chloroform) indicated the reaction was complete. The catalyst was removed by filtration then solvent removal gave a white crystalline solid which was used without further purification. This solid was dissolved in DMF (5 ml) and treated with N-benzyloxycarbonyl-phenylalanine pentafluorophenyl ester (2.62 g, 5.6 mmol) overnight at room temperature. Dichloromethane (30 ml) was added to the reaction mixture and the precipitated product filtered off. The solid (1.47 g) was washed with dichloromethane then dried under vacuum. Further product was recovered from the mother liquors by column chromatography (silica gel, 5% methanol/dichloromethane as eluant) followed by crystallisation. The solids were combined to yield 2.37 g (3.46 mmol, 62%) of the desired product; $^{1}$H NMR: δ ((CD$_{3}$)$_{2}$SO, 323K), 8.27 (1H, d, J=9.0 Hz), 8.09 (1H, br t), 7.82 (1H, d, J=9 Hz), 7.40–7.14 (11H, m), 5.18 (2H, m), 4.96 (2H, m), 4.85 (1H, t), 4.32 (1H, dt, J=4.2, 12.4 Hz), 4.20–3.80 (4H, m), 3.75 (2H, m), 3.10 (1H, dd, J=4.2, 14.0 Hz), 2.80 (1H, dd, J=10.2, 13.8 Hz), 2.00 (3H, s), 1.98 (3H, s), 1.92 (3H, s),and 1.78 (3H, s); $^{13}$C NMR: δ ((CD$_{3}$)$_{2}$SO), 171.4, 169.7, 169.6, 169.2, 169.0, 155.5, 137.9, 136.8, 128.9, 128.0, 127.7, 127.3, 127.1, 125.9, 78.2, 73.0, 72.2, 68.5, 65.1, 61.7, 55.9, 52.1, 41.8, 40.5, 40.1, 39.9, 39.5, 39.2, 38.8, 38.5, 32.3, 22.3, 20.2 and 20.0.

EXAMPLE 1c

[4-(tert-Butoxy)-2R-isobutylsuccinyl]-L-phenylalaninyl-glycinyl-N-(2-acetamido-3,4,6-tri-O-acetyl-2-deoxy-β-D-glucopyranosyl)-amide N-(Benzylcarbonyl)-phenylalaninyl-glycinyl-N-(2-acetamido-3,4,6-tri-O-acetyl-2-deoxy-β-D-glucopyranosyl)-amide (2.37 g, 3.46 mmol) was suspended in methanol (100 ml) and 10% palladium on charcoal (100 mg) added as a slurry in ethyl acetate. Hydrogen gas was bubbled through the solution for 2 hours after which time the suspended solid had dissolved and tic (10% methanol/dichloromethane) indicated the reaction was complete. The catalyst was removed by filtration and solvent removed under reduced pressure to leave a white solid. This amine was dissolved in DMF (5 ml), 2R-isobutylsuccinic acid-1-pentafluorophenyl-4-tert-butyl diester (2.74 g, 6.9 mmol, 2 equivalents) (prepared as described in patent WO 92/13831 ) was added and the mixture was stirred over the weekend at room temperature. The reaction solvent was removed under reduced pressure, the residual oil taken up in dichloromethane and washed with 1M hydrochloric acid, 0.5M sodium carbonate and saturated brine. Purification away from excess pentafluorophenyl ester was achieved by column chromatography (silica gel, dichloromethane and ethyl acetate) to give the desired product (2.33 g, 3.05 mmol, 88%); $^{1}$H NMR: δ ((CD$_{3}$)$_{2}$SO), 7.54 (1H, d, J=8.7 Hz), 7.40 (1H, t, J=5.7 Hz), 7.28–7.12 (6H, m), 6.84 (1H, d, J=8.9 Hz), 5.32–5.17 (2H, m), 5.07 (1H, t, J=9.7 Hz), 4.81 (1H, m), 4.31–3.61 (6H, m), 3.33 (1H, dd, J=5.5, 14.2 Hz), 2.97 (1H, dd, J=9.3, 14.2 Hz), 2.68–2.35 (3H, m), 2.05 (3H, s), 2.04 (3H, s), 2.02 (3H, s), 2.01 (1H, s), 1.54–1.15 (12H, m and s), 0.87 (3H, d, J=6.3 Hz), and 0.81 (3H, d, J=6.3 Hz); $^{13}$C NMR: δ ((CD$_{3}$)$_{2}$SO), 175.0, 172.0, 171.9, 171.8, 170.8, 170.4, 170.2, 169.3, 157.3, 128.1,128.2, 126.4, 80.0, 79.0, 77.5, 77.0, 76.5, 73.0, 72.8, 68.2, 61.8, 55.5, 52.5, 45.3, 41.2, 40.9, 38.0, 36.9, 27.9, 25.4, 23.0, 22.7, 22.1, and 20.5.

EXAMPLE 1d

[4-(Benzyloxyamino)-2R-isobutylsuccinyl]-L-phenylalaninyl-glycinyl-N-(2-acetamido-3,4,6-tri-O-acetyl-2-deoxy-β-D-glucopyranosyl)-amide

[4-(tert-Butoxy)-2R-isobutylsuccinyl]-L-phenylalaninyl-glycinyl-N-(2-acetamido-3,4,6-tri-O-acetyl-2-deoxy-β-D-glucopyranosyl)-amide (2.23 g, 2.9 mmol) in dichloromethane (10 ml) was treated with TFA (5 ml) at room temperature. After stirring overnight at room temperature the solvents were removed under vacuum and the residual oil azeotroped with chloroform in an attempt to remove excess TFA. $^{1}$H NMR analysis indicated complete conversion to the acid and the material was used without further purification. The acid was dissolved in DMF cooled to 0° C., then HOBT (1.33 g, 8.7 mmol), NMM (0.3 g, 2.9 mmol), O-benzylhydroxylamine (1.07 g, 8.7 mmol) and finally EDC (0.83 g, 4.3 mmol) added. The reaction mixture was stirred for six hours, a further portion (0.5 g) of EDC added and the reaction allowed to stir overnight. The reaction was worked up by removing DMF under reduced pressure, redissolving the residue in dichloromethane (200 ml) then washing with 1M hydrochloric acid (2×100 ml), 0.5M sodium carbonate (2×100 ml) and saturated brine. The organic layer was dried over magnesium sulphate, filtered and the solvent removed to leave crude product which was purified by column chromatography (silica gel, 5% methanol/dichloromethane) to give the title compound (1.78 g, 2.19 mmol, 76%); $^1$H NMR: δ (($CD_3)_2SO$, 353K), 10.62 (1H, br s), 7.97 (1H, br d, J=8.4 Hz), 7.79 (2H, br m), 7.63 (1H, br d, J=8.0 Hz), 7.37 (5H, m), 7.23 (5H, m), 5.20 (2H, m), 4.85 (1H, t, J=9.6 Hz), 4.53 (1H, dt, J=5.3, 8.4 Hz), 4.19–3.70 (6H, m), 3.15 (1H, dd, J=5.2, 14.1 Hz), 2.92 (1H, dd, J=9.0, 14.1 Hz), 2.66 (1H, m), 2.17 (1H, dd, J=6.8, 15.0 Hz), 2.02 (1H, m), 1.99 (3H, s), 1.98 (3H, s), 1.93 (3H, s), 1.80 (3H, s), 1.42 (2H, m), 1.09 (1H, m), 0.83 (3H, d, J=6.1 Hz), and 0.79 (3H, d, J=6.1 Hz).

EXAMPLE 1e

[4-(N-Hydroxyamino)-2R-isobutylsuccinyl]-L-phenylalaninyl-glycinyl-N-(2-acetamido-2-deoxy-β-D-glucopyranosyl)-amide

[4-(Benzyloxyamino)-2R-isobutylsuccinyl]-L-phenylalaninyl-glycinyl-N-(2-acetamido-3,4,6-tri-O-acetyl-2-deoxy-β-D-glucopyranosyl)-amide (1.59 g, 1.96 mmol) was dissolved in methanol and sodium methoxide (0.2M in methanol, 0.5 ml) added. After two hours at room temperature tlc (10% methanol/dichloromethane) indicated complete conversion and the reaction was neutralised with an ion exchange resin (Amberlite [Registered Trade Mark] 120/H+). The resin was filtered off, the solvent removed under reduced pressure to leave an amorphous solid. This material was then hydrogenated for 30 minutes in methanol (20 ml) using 10% palladium on charcoal (100 mg) as catalyst to give the title hydroxamic acid as an amorphous solid which was further purified by trituration with ethyl acetate (1.02 g, 1.72 mmol, 87%); Analysis: $C_{27}H_{41}N_5O_{10}$·1.7$H_2O$ requires C, 51.78%, H, 7.15%, N, 11.18%; Found C, 51.64%, H, 6.77%, N, 10.85%; $v_{max}$ (KBr) 3512, 3302, 1654, 1541 cm$^{-1}$; $^1$H NMR: δ (($CD_3)_2SO$, 323K), 10.30 (1H, br s), 7.98 (2H, br m), 7.23 (2H, br m), 7.25–7.14 (5H, m), 4.81 (1H, br dd), 4.53 (1H, m), 3.76–3.36 (6H, m), 3.21–3.08 (3H, m), 2.88 (1H, dd, J=9.6; 13.9 Hz), 2.63 (1H, br m), 2.08–1.90 (2H, br m), 1.86 (3H, s), 1.44–1.29 and 1.10–0.98 (3H, m), 0.79 (3H, d, J=6.3 Hz) and 0.75 (3H, d, J=6.3 Hz); $^{13}$C NMR δ (($CD_3)_2SO$, 323K), 173.8, 171.2, 170.6, 168.9, 167.4, 138.1, 128.9, 127.7, 125.8, 79.1, 78.4, 74.0, 70.5, 60.8, 54.4, 53.6, 42.2, 40.5, 36.7, 35.5, 24.9, 22.9, 22.5, and 21.6.

EXAMPLE 2

[4-(N-Hydroxyamino)-2R-isobutylsuccinyl]-L-phenylalanine-glycinyl-glycinyl-N-(2-acetamido-2-deoxy-β-D-glucopyranosyl)-amide

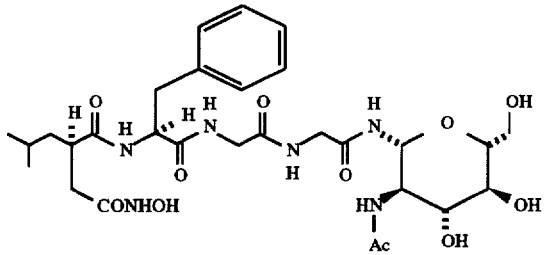

EXAMPLE 2a

N-(Benzyloxycarbonyl)-glycinyl-glycinyl-N-(2-acetamido-3,4,6-tri-O-acetyl-2-deoxy-β-D-glucopyranosyl)-amide N-(Benzyloxycarbonyl)-glycinyl-glycine (3.00 g, 8.67 mmol) and 1-amino-2-acetamido-3,4,6-tri-O-acetyl-2-deoxy-β-D-glucopyranose (2.31 g, 8.67 mmol) were dissolved in DMF (100 ml) and stirred during addition of EEDQ (2.14 g, 8.67 mmol). The reaction mixture was stirred overnight at room temperature. DMF was removed under reduced pressure and the residue partitioned between ethyl acetate and 1M hydrochloric acid. The organic layer was separated and washed with 1M hydrochloric acid, saturated sodium bicarbonate (×3) and brine. The solution was dried over magnesium sulphate, filtered and the solvent removed under vacuum to give the title compound as a white crystalline solid (2.15 g, 3.62 mmol, 42%). $^1$H NMR: δ (($CD_3)_2SO$), 8.34 (1H, d, J=8.7 Hz), 8.12, (1H, brs), 7.99 (1H, d, J=9.0 Hz), 7.37 (1H, br s), 7.36 (5H, s), 5.14 (2H, t, J=9.7 Hz), 5.05 (2H, s), 4.83 (1H, t, J=9.8 Hz), 4.18 (1H, dd, J=12.5, 4.2 Hz), 3.99–3.73 (3H, m), 3.70 (2H, d, J=5.8), 1.99 (3H, s), 1.97 (3H, s), 1.92 (3H, s) and 1.77 (3H, s); $^{13}$C NMR: δ (($CD_3)_2SO$), 170.2, 170.0, 169.5, 169.3, 156.5, 137.0, 128.3, 127.7, 78.3, 72.9, 72.2, 68.5, 65.5, 61.8, 52.0, 43.6, 41.9, 22.5, 20.5 and 20.4.

EXAMPLE 2b

N-(Benzyloxycarbonyl)-phenylalaninyl-glycinyl-glycinyl-N-(2-acetamido-3,4,5-tri-O-acetyl-2-deoxy-β-D-glucopyranosyl)-amide N-(Benzyloxycarbonyl-glycinyl-glycinyl-N-(2-acetamido-3,4,6-tri-O-acetyl-2-deoxy-β-D-glucopyranosyl)-amide (2.05 g, 3.20 mmol) was dissolved in a 1:1 mixture of methanol/ethyl acetate (30 ml) and 10% palladium on charcoal (50 mg) added. Hydrogen gas was passed through the solution for 150 minutes. The catalyst was removed by filtration. Evaporation of solvent under reduced pressure gave a white solid which was used without further purification. The solid was dissolved in DMF (25 ml) and treated with N-benzyloxycarbonyl-phenylalanine pentafluorophenyl ester (1.57 g, 3.38 mmol). The reaction was left to stand at room temperature overnight. DMF was removed under reduced pressure and the residue partitioned between ethyl acetate and 1M hydrochloric acid. The organic layer was separated and washed with 1M hydrochloric acid (×3), saturated sodium bicarbonate (×3) and brine. The solution was dried over magnessium sulphate. Filtration and evaporation of solvent under reduced pressure, followed by recrystallisation from ethyl acetate/hexane gave the desired product as a white crystalline solid (2.30 g, 2.74 mmol, 86%); $^1$H NMR: δ ((CD$_3$)$_2$SO), 8.36 (1H, d, J=9.1Hz), 8.27, (1H, br s), 8.06–7.95 (2H, m), 7.55 (1H, d, J=8.6 Hz), 7.33–7.21 (1 0H, m), 5.14 (2H, t, J=10.0 Hz), 4.94 (2H, d, J=3.7 Hz), 4.83 (1H, t, J=9.7 Hz), 4.31 (1H, m), 4.17 (1H, dd, J=12.6, 4.1 Hz), 3.97–3.69 (7H. m), 3.07 (1H, dd, J=13.8, 3.5 Hz), 2.78 (1H, d, J=13.1 Hz), 1.98 (3H, s), 1.96 (3H, s), 1.91 (3H, s) and 1.77 (3H, s).

EXAMPLE 2c

[4-(tert-Butoxy)-2R-isobutylsuccinyl]-L-phenylalaninyl-glycinyl-glycinyl-N-(2-acetamido-3,4,6-tri-O-acetyl-2-deoxy-β-D-glucopyranosyl)-amide N-(Benzyloxycarbonyl)-phenylalaninyl-glycinyl-glycinyl-N-(2-acetamido-3,4,6-tri-O-acetyl-2-deoxy-β-D-glucopyranosyl)-amide (1.95 g, 2.63 mmol) was dissolved in a 1:1 mixture of methanol/ethyl acetate (20 ml) and 10% palladium on charcoal (50 mg) added. Hydrogen gas was bubbled through the solution for 90 minutes. The catalyst was removed by filtration and solvent removed under reduced pressure to leave a white solid. The amine was dissolved in DMF (25 ml), 2R-isobutylsuccinic acid-1-pentafluorophenyl-4-tert-butyl diester (1.18 g, 2.98 mmol) (prepared as described in patent WO 92/13831) was added and the reaction was stirred at room temperature for 48 hours. The reaction solvent was removed under reduced pressure. The residue was partitioned between ethyl acetate and 1M hydrochloric acid. The organic layer was separated and washed with 1M hydrochloric acid (×2), saturated sodium bicarbonate (×3) and brine before drying over magnesium sulphate, filtration and removal of solvent to leave a colourless oil. Recrystallisation from ethyl acetate/hexane gave the desired product as a white crystalline solid (1.54 g, 1.88 mmol, 71%); $^1$H NMR: δ (CD$_3$OD), 7.23 (5H, m), 5.19 (2H, m), 4.96 (1H, t, J=9.8 Hz), 4.46 (1H, dd, J=8.5, 6.9 Hz), 4.22 (1H, dd, J=12.5, 4.4 Hz), 4.10–3.64 (7H, m), 3.18 (1H, dd, J=13.9, 6.8 Hz), 3.00 (1H, dd, J=13.8, 8.7 Hz), 2.67 (1H, m), 2.37 (1H, dd, J=16.0, 8.4 Hz), 2.21 (1H, dd, J=16.1, 6.1 Hz), 1.96 (3H, s), 1.95 (3H, s), 1.95 (3H, s), 1.87 (3H, s), 1.38 (11 H, m and s), 1.11 (1H, m), 0.84 (3H, d, J=6.3 Hz) and 0.79 (3H, d, J=6.2 Hz); $^{13}$C NMR: δ (CD$_3$OD), 178.0, 174.1, 174.0, 173.2, 172.2, 172.1, 171.7, 171.3, 138.6, 130.3, 129.5, 127.8, 81.0, 79.9, 74.6, 74.5, 69.9, 63.2, 56.9, 53.9, 43.8, 43.5, 42.6, 41.9, 39.2, 37.9, 28.3, 26.6, 23.3, 22.8, 22.6 and 20.6.

EXAMPLE 2d

[4-(Benzyloxyamino)-2R-isobutylsuccinyl]-L-phenylalaninyl)-glycinyl-glycinyl-N-(2-acetamido-3,4,6-tri-O-acetyl-2-deoxy-β-D-glucopyranosyl)-amide

[4-(tert-Butoxy)-2R-isobutylsuccinyl]-L-phenylalaninyl-glycinyl-glycinyl-N-(2-acetamido-3,4,6-tri-O-acetyl-2-deoxy-β-D-glucopyranosyl)-amide (650 mg, 0.79 mmol) was dissolved in trifluoroacetic acid (20 ml) and allowed to stand at room temperature for 4 hours. TFA was removed under reduced pressure and the product was crystallised from dichloromethane/diethyl ether to yield the required product (365 mg, 0.48 mmol, 61%). The acid (150 mg, 0.20 mmol was dissolved in DMF (15 ml) and treated with HOBt (25 mg, 0.20 mmol), O-benzylhydroxylamine (25 mg, 0.20 mmol) and finally EDC (39 mg, 0.20 mmol). The reaction was stirred at room temperature overnight. DMF was removed under reduced pressure. The residue was partitioned between ethyl acetate and 1M hydrochloric acid. The organic layer was separated and washed with 1M hydrochloric acid (×2), satutated sodium bicarbonate (×3) and brine, then dried over magnesium sulphate, filtered and the solvent evaporated to leave a colourless oil. Crystallisation from ethyl acetate/hexane provided the title compound as a white solid (123 mg, 0.14 mmol, 71%); $^1$H NMR: δ (CD$_3$OD), 7.42–7.17 (10H, m), 5.26–5.18 (2H, m), 4.85 (1H, t, J=9.5 Hz), 4.45 (1H, m), 4.28–3.70 (8H, m), 3.15 (1H, dd, J=5.0, 14.1 Hz), 3.02 (1H, dd, J=9.0, 14.2 Hz), 2.68 (1H, m), 2.21 (1H, dd, J=6.9, 14.8 Hz), 2.03 (1H, m), 2.02 (3H, s), 2.00 (3H, s), 1.98 (3H, s), 1.92 (3H, s), 1.35 (2H, m), 1.06 (1H, m), and 0.78 (6H, t, J=6.7 Hz).

EXAMPLE 2e

[4-(N-Hydroxyamino)-2R-isobutylsuccinyl]-L-phenylalaninyl-glycinyl-glycinyl-N-(2-acetamido-2-deoxy-β-D-glucopyranosyl)-amide

[4-(Benzyloxyamino)-2R-isobutylsuccinyl]-L-phenylalaninyl-glycylglycinyl-N-(2-acetamido-3,4,6-tri-O-acetyl-2-deoxy-β-D-glucopyranosyl)-amide (110 mg, 0.13 mmol) was dissolved in methanol (10 ml) and sodium methoxide (8 mg, 0.15 mmol in methanol, 0.5 ml) added. After 3 hours the reaction was neutralised with ion-exchange resin (Amberlite [Registered Trade Mark] 120/H+). The resin was filtered off and washed with methanol. The combined filtrate was treated with 10% palladium on charcoal (50 mg) and stirred under an atmosphere of hydrogen for 90 minutes. Filtration followed by evaporation of solvent gave a white solid. Recrystallisation from methanol/diethyl ether gave the title compound (48 mg, 0.07 mmol, 57%). m.p. 187° C.; $^1$H NMR: δ (CD$_3$OD), 7.25–7.15 (5H, m), 4.89 (1H, m), 4.44 (1H, dd, J=9.2, 6.0 Hz), 4.01–3.43 (11 H, m), 3.24 (1H, m), 3.04 (1H, dd, J=13.8, 9.5 Hz), 2.66 (1H, m), 2.24 (1H, dd, J=14.8, 5.9 Hz), 2.08 (1H, dd, J=14.5, 5.9 Hz), 1.95 (3H, s), 1.36 (2H, m), 1.07 (1H, m), and 0.77 (6H, t, J=6.7 Hz); $^{13}$C NMR: δ (CD$_3$OD), 178.0, 174.7, 174.2, 172.4, 170.8, 138.8, 130.2, 129.5, 126.7, 80.62, 79.7, 77.3, 71.9, 62.6, 56.9, 55.9, 43.9, 43.6, 42.5, 37.6, 26.6, 23.5, 22.9 and 22.3.

EXAMPLE 3

[4-(N-Hydroxyamino)-2R-isobutylsuccinyl]-O-[(2-acetamido-2-deoxy-β-D-glucopyranosyl) carboxamidomethyl]-L-tyrosine-N-methylamide

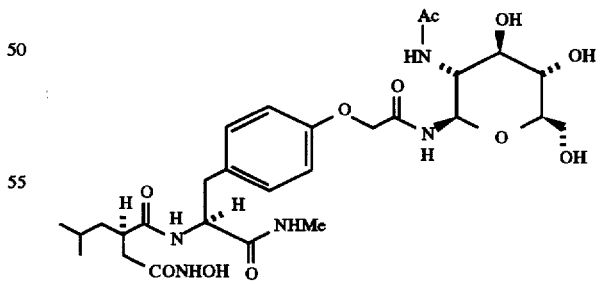

EXAMPLE 3a

[4-tert-Butoxy-2R-isobutylsuccinyl]-O-[(2-acetamido-2-deoxy-β-D-glucopyranosyl) carboxamidomethyl]-L-tyrosine-N-methylamide

[4-tert-Butoxy-2R-isobutylsuccinyl]-O-carboxymethyl-L-tyrosine-N-methylamide (prepared as described in patent WO 92/13831, 900 mg, 1.94 mmol), 1-amino-2-acetamido-3,4,6-tri-O-acetyl-2-deoxy-β-D-glucopyranose (671 mg, 1.94 mmol) and EEDQ (478 mg, 1.94 mmol) were dissolved in dichloromethane (20 ml). The reaction mixture was stirred overnight at room temperature resulting in formation of a gelatinous precipitate. Solvent was removed under reduced pressure and the residue partitioned between ethyl acetate (50 ml) and 1M hydrochloric acid (50 ml). The organic layer was separated, washed with 1M hydrochloric acid (2×50 ml) and brine (50 ml). On standing for 10 minutes a thick white precipitate formed which was collected by filtration, washed with diethyl ether and dried under vacuum to yield the title compound (925 mg, 1.17 mmol, 60%); $^1$H NMR: δ ((CD$_3$)$_2$SO), 8.66 (1H, d, J=8.9 Hz), 8.10 (1H, d, J=8.2 Hz), 8.04 (1H, d, J=8.9 Hz), 7.81 (1H, m), 7.11 (2H, d, J=8.4 Hz), 6.79 (2H, d, J=8.5 Hz,), 5.27–5.13 (2H, m), 4.84 (1H, t, J=9.7 Hz), 4.44 (2H, s), 4.35 (1H, dd, J=14.7, 8.3 Hz), 4.19 (1H, dd, J=12.6, 4.3 Hz), 4.02–3.86 (3H, m), 2.88 (1H, dd, J=13.8, 5.6 Hz), 2.71 (1H, dd, J=13.8, 8.7 Hz), 2.60 (1H, m), 2.52 (1H, d, J=7.4 Hz), 2.26 (1H, dd, J=15.7, 7.3 Hz), 2.09 (1H, dd, J=15.6, 7.2 Hz), 1.99 (3H, s), 1.97 (3H, s), 1.92 (3H, s), 1.71 (3H, s), 1.35 (11 H, s and m), 0.82 (3H, d, J=6.1 Hz), and 0.75 (3H, d, J=6.0 Hz); $^{13}$C NMR: δ ((CD$_3$)$_2$SO), 173.6, 171.3, 170.8, 170.0, 169.5, 169.3, 168.5, 130.0, 114.4, 79.7, 78.2, 72.9, 72.4, 68.8, 62.0, 54.2, 52.2, 38.0, 36.7, 27.7, 25.4, 24.1, 22.9, 22.5, 22.2, 20.5 and 20.2.

EXAMPLE 3b

[4-Hydroxy-2R-isobutylsuccinyl]-O-[(2-acetamido-2-deoxy-β-D-glucopyranosyl)carboxamidomethyl]-L-tyrosine-N-methylamide

[4-tert-Butoxy-2R-isobutylsuccinyl]-O-[(2-acetamido-2-deoxy-β-D-glucopyranosyl)carboxamidomethyl]-L-tyrosine-N-methylamide (250 mg, 0.32 mmol) was dissolved in a mixture of TFA and dichloromethane (1:1, 10 ml) and allowed to stand at room temperature overnight. Solvent was removed under reduced pressure. Addition of diethyl ether (30 ml) gave a white solid which was collected by filtration, washed with diethyl ether (2×30 ml) and dried under vacuum to give the title compound (230 mg, 3.0 mmol, 100%), $^1$H NMR: δ ((CD$_3$)$_2$SO), 8.63 (1H, d, J=8.8 Hz), 8.03–7.98 (2H, m), 7.71 (1H, m), 7.11 (2H, d, J=8.5 Hz), 6.80 (2H, d, J=8.3 Hz), 5.24 (1H, t, J=9.2 Hz), 5.18 (1H, t, J=10.2 Hz), 4.45 (2H, s), 4.35 (1H, m), 4.19 (1H, dd, J=12.6, 4.3 Hz), 4.03–3.86 (3H, m), 2.89 (1H, dd, J=13.8, 5.7 Hz), 2.74 (1H, dd, J=13.7, 8.5 Hz), 2.65 (1H, m), 2.54 (3H, d, J=4.3 Hz), 2.30 (1H, dd, J=1 6.0, 7.5 Hz), 2.14 (1H, dd, J=1 6.1, 6.7 Hz), 1.99 (3H, s), 1.97 (3H, s), 1.92 (3H, s), 1.72 (3H, s), 1.34 (2H, m), 1.06 (1H, m), 0.82 (3H, d, J=6.0 Hz) and 0.76 (3H, d, J=6.0 Hz); $^{13}$C NMR: δ ((CD$_3$)$_2$SO), 173.8, 173.1, 171.2, 170.0, 169.5, 169.3, 168.5, 156.2, 130.8, 130.0, 114.4, 78.2, 72.9, 72.4, 68.7, 66.9, 61.9, 54.1, 52.2, 37.0, 36.6, 25.5, 24.1, 22.9, 22.5, 20.5 and 20.3.

EXAMPLE 3c

[4-(N-Benzyloxyamino)-2R-isobutylsuccinyl]-O-[(2-acetamido-2-deoxy-β-D-glucopyranosyl)carboxamidomethyl]-L-tyrosine-N-methylamide

[4-Hydroxy-2R-isobutylsuccinyl]-O-[(2-acetamido-2-deoxy-β-D-glucopyranosyl)carboxamidomethyl]-L-tyrosine-N-methylamide (950 mg, 1.29 mmol) was taken up in DMF (15 ml) and treated with HOBt (174 mg, 1.29 mmol) and EDC (742 mg, 3.87 mmol). After stirring at room temperature for 30 minutes the reaction was treated with O-benzyl hydroxylamine (476 mg, 3.87 mmol) and allowed to stir overnight. The reaction solvent was removed under reduced pressure to leave a colourless gum. Addition of 1M hydrochloric acid (20 ml) and diethyl ether (20 ml) gave a white precipitate. The solid was collected by filtration, washed with distilled water (3×20 ml) and diethyl ether (3×20 ml) before drying under vacuum to provide the title compound (810 mg, 0.96 mmol, 75%); $^1$H NMR: δ ((CD$_3$)$_2$SO), 8.51 (1H, br m), 7.91 (2H, br m), 7.73 (1H, br m), 7.37 (5H, s), 7.11 (2H, d, J=8.4 Hz), 6.79 (2H, d, J=8.0 Hz), 5.26–5.14 (2H, m), 4.84 (1H, t, J=9.6 Hz), 4.77 (2H, s), 4.43 (2H, s), 4.37 (1H, m), 4.17 (1H, rid, J=12.4, 4.1 Hz), 4.00–3.84 (3H, m), 2.99–2.91 (1H, m), 2.81–2.75 (1H, m), 2.64 (1H, m), 2.57 (3H, d, J=4.2 Hz), 2.00 (2H, m), 1.99 (3H, s), 1.97 (3H, s), 1.93 (3H, s), 1.73 (3H, s), 1.33 (2H, m), 1.02 (1H, m), 0.79 (3H, d, J=6.0 Hz) and 0.74 (3H, d, J=5.9 Hz).

EXAMPLE 3d

[4-(N-Hydroxyamino)-2R-isobutylsuccinyl]-O-[(2-acetamido-2-deoxy-β-D-glucopyranosyl)carboxamidomethyl]-L-tyrosine-N-methylamide

[4-(N-Benzyloxyamino)-2R-isobutylsuccinyl]-O-[(2-acetamido-2-deoxy-β-D-glucopyranosyl)carboxamidomethyl]-L-tyrosine-N-methylamide (780 mg, 0.93 mmol) was suspended in methanol (25 ml) and sodium methoxide (0.93 mmol) in methanol (5 ml) added. The reaction was allowed to stir at room temperature overnight. The reaction was neutralised with ion exchange resin (Amberlite [Registered Trade Mark] 120/H+). The solution/suspension was decanted from the resin. The reaction mixture was treated with 10% palladium on charcoal (100 mg) and stirred under an atmosphere of hydrogen for 60 minutes. The catalyst was removed by filtration and solvent was removed under reduced pressure to give a white solid. Recrystallisation from methanol/diisopropyl ether gave the title compound (432 mg, 0.69 mmol, 74%). m.p. 222.6° C.; Analysis: C$_{28}$H$_{43}$N$_3$O$_{11}$.1.3H$_2$O requires C, 51.81%, H, 7.08%, N, 10.79%; Found C, 51.78%, H, 7.05%, N, 10.77%; $^1$H NMR: δ ((CD$_3$)$_2$SO), 10.40 (1H, s), 8.76 (1H, s), 8.44 (1H, d, J=8.3 Hz), 8.00 (1H, d, J=8.2 Hz), 7.93–7.85 (2H, m), 7.12 (2H, d, J=8.4 Hz), 6.82 (2H, d, J=8.5 Hz), 4.78 (1H, t, J=9.0 Hz), 4.47–4.32 (3H, m), 3.68–3.34 (6H, m), 3.14 (2H, s), 2.90 (1H, dd, J=14.0, 5.1 Hz), 2.74 (1H, dd, J=13.5, 9.5 Hz), 2.56 (3H, d, J=4.3 Hz), 2.55 (1H, m), 2.05 (1H, dd, J=14.3, 6.9 Hz), 1.90 (1H, dd, J=14.3, 7.6 Hz), 1.76 (3H, s), 1.27 (2H, m), 0.96 (1H, m), 0.78 (3H, d, J=6.2 Hz) and 0.73 (3H, d, J=6.4 Hz); $^{13}$C NMR: δ ((CD$_3$)$_2$SO), 173.6, 171.4, 170.7, 168.5, 167.7, 156.1, 131.0, 130.0, 114.3, 79.2, 78.7, 73.9, 70.5, 66.8, 60.8, 54.3, 54.2, 40.6, 36.4, 35.7, 25.6, 25.1, 23.2, 22.7 and 21.9.

EXAMPLE 4

[3S-Hydroxy-4-(N-hydroxyamino)-2R-isobutylsuccinyl]-L-phenylalaninyl-glycinyl-N-(2-acetamido-2-deoxy-β-D-glucopyranosyl)-amide

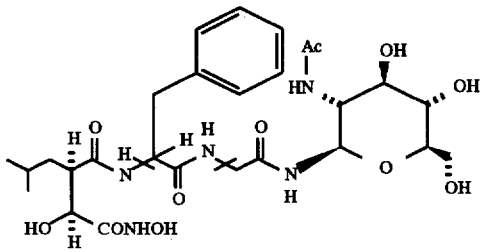

EXAMPLE 4a

[2R-(2,2-Dimethyl-1,3-dioxalon-5S-yl)-4-methylpentanoyl]-L-phenylalaninyl-glycinyl-N-(2-acetamido-3,4,6-tri-O-acetyl-2-deoxy-β-D-glucopyranosyl)-amide N-(Benzyloxycarbonyl)-phenylalaninyl-glycinyl-N-(2-acetamido-3,4,6-tri-O-acetyl-2-deoxy-β-D-glucopyranosyl)-amide (Example 1b, 1.15 g, 1.68 mmol) was suspended in methanol (30 ml) and treated with 10% palladium on charcoal (100 mg). The reaction mixture was stirred under an atmosphere of hydrogen for 60 minutes. The catalyst was removed by filtration and solvent evaporated to give a white solid. The amine was dissolved in DMF (15 ml) and treated with 2R-(2,2-dimethyl-4-oxo-1,3-dioxalan5S-yl)-4-methylpentanoic acid pentafluorophenyl ester (1.33g, 2.26 mmol) (prepared as described in patent WO 94/02447). The reaction mixture was left standing at room temperature overnight. DMF was removed under reduced pressure to leave a colourless oil which was partitioned between ethyl acetate and saturated sodium bicarbonate. The organic layer was separated and washed with saturated sodium bicarbonate (×2) and brine before drying over magnesium sulphate. Filtration and removal of solvent and recrystallisation from ethyl acetate and hexane gave the title compound (825 mg, 1.08 mmol, 64%); $^1$H NMR: δ (CD$_3$OD), 7.22 (5H, s), 5.26–5.19 (2H, m), 4.98 (1H, t, J=10.0 Hz), 4.57 (1H, dd, J=9.3, 5.4 Hz), 4.51 (1H, d, J=8.1 Hz), 4.24 (1H, dd, J=12.4, 4.3 Hz), 4.06–3.75 (3H, m), 3.22 (1H, m), 3.06–3.01 (1H, m), 2.70 (1H, m), 1.98 (3H, s), 1.97 (3H, s), 1.95 (3H, s), 1.89 (3H, s), 1.59 (2H, m), 1.49 (3H, s), 1.45 (3H, s), 1.20 (1H, m), 0.84 (3H, d, J=6.6 Hz) and 0.80 (3H, d, J=6.5 Hz).

EXAMPLE 4b 3S,4-Dihydroxy-2R-isobutylsuccinyl-L-phenylalaninyl-glycinyl-N-(2-acetamido 3,4,6-tri-O-acetyl-2-deoxy-β-D-glucopyranosyl)-amide

[2-R-(2,2-Dimethyl-1,3-dioxalon-5S-yl)-4-methylpentanoyl]-L-phenylalaninyl-glycinyl-N-(2-acetamido-3,4,6-tri-O-acetyl-2-deoxy-β-D-glucopyranosyl)-amide (300 mg, 0.39 mmol) was dissolved in a mixture of TFA/dichloromethane (1:1, 20 ml). The reaction mixture was allowed to stand at room temperature overnight. Solvent and excess TFA were removed under reduced pressure. Addition of diethyl ether (50 ml) gave a white solid which was collected by filtration. The solid was washed with diethyl ether and dried under vacuum to yield the title compound (265 mg, 0.37 mmol, 94%); $^1$H NMR: δ ((CD$_3$)$_2$SO), 8.33 (1H, d, J=9.3 Hz), 8.04–9.94 (2H, m), 7.23 (5H, s), 5.21–5.10 (2H, m), 4.83 (1H, t, J=9.7 Hz), 4.52 (1H, m), 3.48 (1H, br s), 4.20 (1H, m), 3.98–3.68 (5H, m), 3.15–2.90 (2H, m), 2.58 (1H, m), 1.99 (3H, s), 1.97 (3H, s), 1.92 (3H, s) 1.77 (3H, s), 1.48 (1H, m), 1.25 (1H, m), 1.06 (1H, m), 0.79 (3H, d, J=5.7 Hz) and 0.75 (3H, d, J=6.4 Hz).

EXAMPLE 4c

[3S-Hydroxy-4-(N-benzyloxyamino)-2R-isobutylsuccinyl]-L-phenylalaninyl-glycinyl-N-(2-acetamido-3,4,6-tri-O-acetyl-2-deoxy-β-D-glucopyranosyl)-amide

[3S,4-Dihydroxy-2R-isobutylsuccinyl]-2-phenylalaninyl-glycinyl-N-(2-acetamido-3,4,6-tri-O-acetyl-2-deoxy-β-D-glucopyranosyl)-amide (250 mg, 0.35 mmol) was dissolved in a mixture of THF/water (1:1, 20 ml). The solution was treated with O-benzylhydroxylamine hydrochloride (88 mg, 0.55 mmol) and EDC (140 mg, 0.73 mmol). The reaction was stirred at room temperature overnight. THF was removed under reduced pressure. A white precipitate formed which was collected by filtration, washed with water (50 ml) and dried under vacuum to yield the title compound (195 mg, 0.24 mmol, 67%); $^1$H NMR: δ ((CD$_3$)$_2$SO), 8.33 (1H, d, J=9.0 Hz), 8.17 (1H, d, J=6.3 Hz), 7.99–7.90 (2H, m), 7.39–7.36 (5H, m), 7.24–7.18 (6H, m), 5.67 (1H, d, J=6.2 Hz), 5.20–5.10 (2H, m), 4.84 (1H, t, J=9.8 Hz), 4.76 (2H, s), 4.53 (1H, m), 4.16 (1H, dd, J=12.2, 4.4 Hz), 3.97–3.82 (3H, m), 3.70 (2H, t, J=6.0 Hz), 3.11 (1H, dd, J=14.6, 5.3 Hz), 2.91 (1H, dd, J=14.1, 9.0 Hz), 2.54 (1H, m), 1.98 (3H, s), 1.97 (3H, s), 1.92 (3H, s), 1.78 (3H, s), 1.43 (1H, m), 1.35 (1H, m), 0.93 (1H, m) and 0.74 (6H, dd, J=4.5 Hz).

EXAMPLE 4d

[3S-Hydroxy-4-(N-hydroxyamino)-2R-isobutylsuccinyl]-L-phenylalaninyl-glycinyl-N-(2-acetamido-2-deoxy-β-D-glucopyranosyl)-amide A suspension of [3S-hydroxy-4-(N-benzyloxy-amino)-2R-isobutylsuccinyl]-L-phenylalaninyl-glycinyl-N-(2-acetamido-3,4,6-tri-O-acetyl-2-deoxy-β-D-glucopyranosyl)-amide (160 mg, 0.19 mmol)in methanol (15 ml) was treated with a solution of sodium methoxide (5 mg, 0.22 mmol) in methanol (5 ml). The reaction was neutralised with ion exchange resin (Amberlite [Registered Trade Mark] 120/H+) and the supernatent was decanted. The reaction mixture was treated with 10% palladium on charcoal (50 mg) and stirred under an atmosphere of hydrogen for 60 minutes. The catalyst was removed by filtration and solvent removed under reduced pressure to leave a white solid. Recrystallisation from methanol/diisopropyl ether gave the title compound (75 mg, 0.12 mmol, 63%).; Mpt 200.5° C.; $^1$H NMR: δ ((CD$_3$)$_2$SO), 10.40 (1H, s), 8.27 (1H, m), 7.99–7.89 (4H, m), 7.22 (5H, m), 4.76 (1H, t, J=9.1 Hz), 4.52 (1H, m), 3.86 (1H, d, J=6.8 Hz), 3.75–3.32 (6H, m), 3.12 (3H, m), 2.94 (1H, m), 2.50 (1H, m), 1.66–1.55(1H, m), 1.32–1.15(1H, m), 1.04–0.90(1H, m), 0.74(3H, d, J=6.2 Hz) and 0.73 (3H, d, J=6.4 Hz); $^{13}$C NMR: δ ((CD$_3$)$_2$SO), 172.5, 171.3, 170.7, 169.2, 168.7, 138.3, 129.0, 127.9, 126.0, 79.3, 78.6, 74.0, 71.0, 70.4, 60.8, 54.3, 53.8, 42.4, 37.4, 36.7, 24.9, 23.5, 22.7 and 21.5.

EXAMPLE 5

[3S-Allyl-4-(N-hydroxyamino)-2R-isobutylsuccinyl]
-N4-(2-acetamido-2-deoxy-β-D-glucopyranosyl)-L-
glutamine-N-methylamide

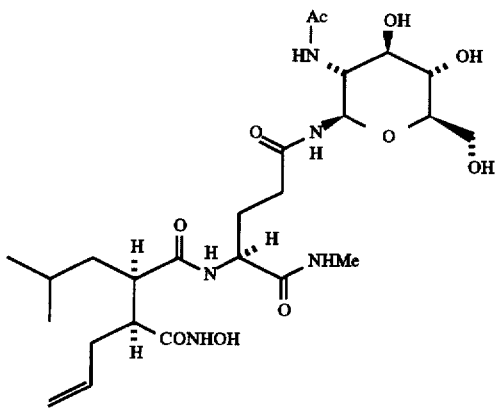

EXAMPLE 5a

N<sup>α</sup>-tert-Butyloxycarbonyl-N<sup>4</sup>-(2-acetamido-3,4,6-
tri-O-acetyl-2-deoxy-α-D-glucopyranosyl)-L-
glutamine-N-methylamide Prepared by methods analogous to those described in Example 1 a, starting from N<sup>α</sup>-tert-butyloxycarbonyl-L-glutamic acid-N-methylamide (2.80 g, 10.75 mmol) and 2-acetamido-3,4,6-tri-O-acetyl-2-deoxy-α-D-glucopyranosylamine (10.75 mmol). Yield: 3.95 g (64%). ¹H-NMR; δ ((CD₃)₂SO), 8.47 (1H, d, J=9.2 Hz), 7.80 (1H, d, J=9.0 Hz), 7.70 (1H, br m), 6.82 (1H, br d), 5.18–5.05 (2H, m), 4.80 (1H, t, J=9.8 Hz), 4.21–4.14 (1H, m), 3.96–3.67 (4H, m), 2.57 (3H, d, J=4.2 Hz), 2.18–2.07 (2H, m), 1.99 (3H, s), 1.96 (3H, s), 1.90 (3H, s), 1.73 (3H, s), 1.73–1.62 (2H, m), 1.37 (9H, s); ¹³C-NMR; δ ((CD₃)₂SO), 172.2, 172.0, 169.9, 169.4, 169.2, 78.1, 73.4, 72.3, 68.7, 62.0, 53.9, 52.3, 31.9, 28.2, 27.9, 25.5, 22.5, 20.5 and 20.3.

EXAMPLE 5b

[3S-allyl-4-tert-butoxy-2R-isobutylsuccinyl]-N<sup>4</sup>-(2-
acetamido-3,4,6-tri-O-acetyl-2-deoxy-α-D-
glucopyranosyl)-L-glutamine-N-methylamide Prepared by methods analogous to those described in Example 1c, starting from 3R,S-allyl-2R-isobutylsuccinic acid-1-pentafluorophenyl-4-tert-butyl diester (3:1, RS:RR) (prepared as described in patent WO 94/21625, 4.3 g, 10.1 mmol) and N<sup>α</sup>-tert-butyloxycarbonyl-N<sup>4</sup>-(2-acetamido-3,4,6-tri-O-acetyl-2-deoxy-α-D-glucopyranosyl)-L-glutamine-N-methylamide (5.9 g, 10.1 mmol). The crude product was purified by recrystallising twice from ethyl acetate-hexane. Yield: 2.45 g (33%). ¹H-NMR; δ ((CD₃)₂SO), 8.44 (1H, d, J=9.3 Hz), 8.20 (1H, d, J=7.8 Hz), 7.89 (1H, d, J=9.3 Hz), 7.67 (1H, br m), 5.70–5.63 (1H, m), 5.18–4.95 (4H, m), 4.81 (1H, t, J=9.8 Hz), 4.22–4.14 (2H, m), 3.97–3.79 (4H, m), 2.58 (3H, d, J=4.5 Hz), 2.33–2.27 (1H, m), 2.20–2.02 (5H, m), 1.99 (3H, s), 1.96 (3H, s), 1.91 (3H, s), 1.90–1.85 (2H, m), 1.73 (3H, s), 1.55–1.46 (1H, m), 0.84 (3H, d, J=6.4 Hz), 0.78 (3H, d, J=6.6 Hz).

EXAMPLE 5c

3S-Allyl-4-hydroxy-2R-isobutylsuccinyl-N<sup>4</sup>-(2-
acetamido-3,4,6-tri-O-acetyl-2-deoxy-α-D-
glucopyranosyl)-L-glutamine-N-methylamide

[3S-Allyl-4-tert-butoxy-2R-isobutylsuccinyl]-N<sup>4</sup>-(2-
acetamide-3,4,6-tri-O-acetyl-2-deoxy-α-D-glucopyranosyl)
-L-glutamine-N-methylamide (2.2 g, 3.0 mmol) was deprotected by TFA acidolysis, as described in Example 1d. Recrystallisation from methanol/diisopropyl ether afforded the title compound as a white solid. Yield: 950 mg (47%). ¹H-NMR; δ ((CD₃)₂SO), 8.44 (1H, d, J=9.3 Hz), 8.19 (1H, d, J=7.7 Hz), 7.89 (1H, d, J=9.1 Hz), 7.65 (1H, br m), 5.75–5.64 (1H, m), 5.18–4.94 (4H, m), 4.81 (1H, t, J=9.8 Hz), 4.20–4.14 (2H, m), 3.97–3.80 (4H, m), 2.58 (3H, d, J=4.5 Hz), 2.40–2.32 (1H, m), 2.19–1.90 (5H, m), 1.99 (3H, s), 1.96 (3H, s), 1.91 (3H, s), 1.73 (3H, s), 1.58–1.38 (2H, m), 0.95 (1H, m), 0.83 (3H, d, J=6.5 Hz), 0.78 (3H, d, J=6.6 Hz).

EXAMPLE 5d

[3S-Allyl-4-(N-hydroxyamino)-2R-isobutylsuccinyl]
-N4-(2-acetamido-3,4,6-tri-O-acetyl-2-deoxy-α-D-
glucopyranosyl)-L-glutamine-N-methylamide To a solution of [3S-allyl-4-hydroxy-2R-isobutylsuccinyl]-N4-(2-acetamido-3,4,6-tri-O-acetyl-2-deoxy-α-D-glucopyranosyl)-L-glutamine-N-methylamide (920 mg, 1.35 mmol) in DMF (20 ml) was added HOBt (200 mg, 1.48 mmol) EDC (335 mg, 1.75 mmol) and the mixture was stirred for 90 minutes at room temperature. Hydroxylamine hydrochloride (111 mg, 1.60 mmol) was added followed by NMM (177 mg, 1.75 mmol) and stirring was continued overnight. The solvent was removed under reduced pressure. Trituration with diethyl ether and water gave a white solid which was collected by filtration and recrystallised from methanol/diisopropyl ether. Yield: 675 mg (72%). ¹H-NMR; δ ((CD₃)₂SO), 10.4 (1H, s), 8.71 (1H, s), 8.45 (1H, d, J=9.6 Hz), 8.13 (1H, d, J=7.8 Hz), 7.88 (1H, br m), 5.61–5.58 (1H, m), 5.16–4.78 (4H, m), 4.81 (1H, t, J=9.8 Hz), 4.20–4.15 (2H, m), 3.97–3.80 (4H, m), 2.57 (3H, d, J=4.4 Hz), 2.24–2.05 (5H, m), 1.99 (3H, s), 1.96 (3H, s), 1.90 (3H, s), 1.75 (1H, m), 1.73 (3H, s), 1.50 (2H, m), 0.98–0.95 (1H, m), 0.81 (3H, d, J=6.5 Hz), 0.77 (3H, d, J=6.3 Hz).

EXAMPLE 5e

[3S-Allyl-4-(N-hydroxyamino)-2R-isobutylsuccinyl]
-N4-(2-acetamido-2-deoxy-α-D-glucopyranosyl)-L-
glutamine-N-methylamide

[3S-Allyl-4-(N-hydroxyamino)-2R-isobutylsuccinyl]-N4-(2-acetamido-3,4,6-tri-O-O-acetyl-2-deoxy-α-D-glucopyranosyl)-L-glutamine-N-methylamide (650 mg, 0.93 mmol) was O-deacetylated as described in Example 1 e. The product was recrystallised from methanol-diisopropyl ether. Yield: 251 mg (47%). m.p. 232°–234° C. ¹H-NMR; δ ((CD₃)₂SO), 10.42 (1H, s), 8.13 (1H, d, J=7.9 Hz) 7.95 (1H, d, J=8.9 Hz), 7.77 (1H, d, J=4.7 Hz), 5.60 (1H, m), 4.94 (2H, m), 4.80 (1H, t, J=9.3 Hz), 4.20 (1H, m), 3.66–3.30 (5H, m), 3.08 (2H, d, J=6.4 Hz), 2.58 (3H, d, J=4.5 Hz), 2.24–1.99 (4H, m), 1.96–1.91 (1H, m), 1.86–1.70 (4H, m and s), 1.45–1.39 (2H, m), 0.97–0.93 (1H, m), 0.82 (3H, d, J=6.4 Hz), and 0.77 (3H, d, J=6.3 Hz). 13C-NMR; δ ((CD₃)₂SO), 173.5, 172.1, 171.5, 170.2, 169.4, 135.9, 116.4, 79.2, 78.8, 74.6, 70.8, 61.1, 54.8, 52.4, 46.1, 45.9, 34.8, 32.3, 27.9, 25.6, 25.3, 24.2, 22.9 and 21.6.

BIOLOGICAL EXAMPLE A

The potency of compounds of the invention as inhibitors of collagenase was determined by the procedure of Cawston and Barrett, (*Anal. Biochem.*, 99, 340–345, 1979), hereby incorporated by reference, whereby a 1 mM solution of the compound being tested, or a dilution thereof, was incubated at 37° C. for 16 hours with collagen and collagenase (buffered with 25 mM Hepes [Registered Trade Mark], pH 7.5 containing 5 mM $CaCl_2$, 0.05% Brij [Registered Trade Mark] 35 and 0.02% $NAN_3$). The collagen Was acetylated 14C collagen prepared by the method of Cawston and Murphy, (Methods in Enzymology, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity ($IC_{50}$).

The potency of compounds of the invention as inhibitors of stromelysin was determined by the procedure of Cawston et al, (Biochem. J., 195, 159–165, 1981), hereby incorporated by reference, whereby a 1 mM solution of the compound being tested, or a dilution thereof, was incubated at 37° for 16 hours with stromelysin and $^{14}C$ acetylate casein (buffered with 25 mM Hepes [Registered Trade Mark], pH 7.5 containing 5 mM $CaCl_2$, 0.05% Brij [Registered Trade Mark] 35 and 0.02% $NAN_3$). The casein was acetylated $^{14}C$ casein prepared by the method of Cawston et al (ibid). The stromelysin activity in the presence of 1 mM of the test compound, or a dilution thereof, was compared to activity in a control devoid of inhibitor and the result reported below as that of inhibitor concentration effecting 50% inhibition of the stromelysin activity ($IC_{50}$).

Results:

| Compound | Collagenase $IC_{50}$ (nM) | Stromelysin $IC_{50}$ (nM) |
| --- | --- | --- |
| Example 3 | 20 | 600 |

BIOLOGICAL EXAMPLE B

The ability of example compounds of the invention to inhibit the release of TNF was investigated. The assay is based on the ability of phorbol myristate acetate (PMA) to stimulate the release of TNF α from a human monocytic cell line, U937.

U937 cells cultured in RPMI (Rosewall Park Memorial Institute) 1640 medium+5% foetal calf serum are centifuged at 1000×g for 5 minutes and then resuspended in medium at 2×10$^6$/ml. 1 ml of cell suspension is aliquoted into individual wells of 24-well plates. Test compounds are dissolved in dimethyl sulphoxide (DMSO) at a stock concentration of 100 mM, then diluted to 50× the final required concentration with RPMI 1640 medium. 20 μl of the diluted compounds are added to U937 cells in duplicate wells. TNF α release is stimulated by addition of PMA to the cells at a final concentration of 50 nM. Appropriate control cultures are set up in duplicate. The plates are incubated for 18 hours at 37° C., 5% $CO_2$, then centrifuged at 1000×g for 5 minutes. A specific ELISA for TNF α obtained from R&D Systems Europe Ltd, Abingdon, England is used to measure TNF α levels in the culture supernatants The average concentration of test compound which inhibits the release of TNF α by 50% relative to the control culture was assessed. The compound of example 5 above had $IC_{50}$ value less than 3.5 μM. μM.

We claim:

1. A compound of the formula (I)

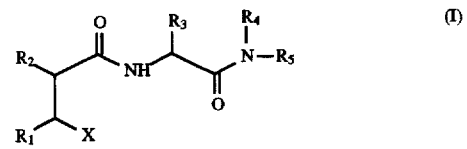

or a pharmaceutically acceptable salt, hydrate or solvate thereof, wherein;

X is —CONHOH;

$R_1$ is hydrogen, hydroxyl, or allyl;

$R_2$ is iso-butyl, n-octyl, or phenylpropyl;

$R_3$ is (a) a group —($C_1$-$C_6$ alkyl)$COR_6$, or —($C_1$-$C_6$ alkyl)($C_6H_4$)$XR_6$ where X is a group —$OCH_2CO$, and $R_6$ is a group of formula (II):

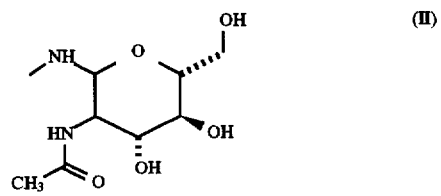

or (b) $R_3$ is benzyl or t-butyl;

$R_4$ is (i) a group —(CH($R_7$)CONH)$_m$$COR_6$, where m=1 or 2, $R_6$ is as defined above, and $R_7$ is hydrogen; or (ii) hydrogen, methyl, or ethyl; and $R_5$ is hydrogen, methyl, or ethyl;

provided that at least one of the groups $R_3$ and $R_4$ contains a group $R_6$ as defined above.

2. A compound selected from the group consisting of;

[4-(N-Hydroxyamino)-2R-isobutylsuccinyl]-L-phenylalaninyl-glycinyl-N-(2-acetamido-2-deoxy-β-D-glucopyranosyl)-amide;

[4-(N-Hydroxyamino)-2R-isobutylsuccinyl]-L-phenylalaninyl-glycinyl-glycinyl-N-(2-acetamido-2-deoxy-β-D-glucopyranosyl)-amide;

[4-(N-Hydroxyamino)-2R-isobutylsuccinyl]-O-[(2-acetamido-2-deoxy-β-D-glucopyranosyl)carboxamidomethyl]-L-tyrosine-N-methylamide;

3S-Hydroxy-4-(N-hydroxyamino)-2R-isobutylsuccinyl-L-phenylalaninyl-glycinyl-N-(2-acetamido-2-deoxy-β-D-glucopyranosyl)-amide;

and salts, solvates and hydrates thereof.

3. [3S-Allyl-4-(N-hydroxyamino)-2R-isobutylsuccinyl]-N4-(2-acetamido-2-deoxy-α-D-glucopyranosyl)-L-glutamine-N-methylamide and salts, solvates and hydrates thereof.

4. A pharmaceutical or veterinary composition comprising a compound as claimed in any one of claims 1, 2 or 3 together with a pharmaceutically or veterinarily acceptable excipient or carrier.

5. A pharmaceutical or veterinary composition as claimed in claim 4 which is adapted for oral administration.

6. A compound as claimed in claim 1 except that one or more of the hydroxy groups in the group $R_6$ is protected.

7. A compound as claimed in claim 6 in which the said hydroxy groups are protected as the acetate.

* * * * *